(12) United States Patent
Kanellakopulos et al.

(10) Patent No.: US 6,177,431 B1
(45) Date of Patent: Jan. 23, 2001

(54) TETRAHYDROPYRIMIDINE DERIVATIVES

(75) Inventors: Johannes Kanellakopulos, Dormagen; Detlef Wollweber, Wuppertal; Christoph Erdelen, Leichlingen, all of (DE)

(73) Assignee: Bayer Aktiengesellschaft, Leverkusen (DE)

( * ) Notice: Under 35 U.S.C. 154(b), the term of this patent shall be extended for 0 days.

(21) Appl. No.: 09/125,998

(22) PCT Filed: Feb. 19, 1997

(86) PCT No.: PCT/EP97/00775

§ 371 Date: Aug. 28, 1998

§ 102(e) Date: Aug. 28, 1998

(87) PCT Pub. No.: WO97/32878

PCT Pub. Date: Sep. 12, 1997

(30) Foreign Application Priority Data

Mar. 4, 1996 (DE) ................................. 196 08 243
Dec. 11, 1996 (DE) ................................. 196 51 429

(51) Int. Cl.$^7$ .......................... C07D 487/04; A01N 43/90
(52) U.S. Cl. ......................... 514/258; 546/112; 546/113
(58) Field of Search ................... 546/112, 113; 514/258

(56) References Cited

U.S. PATENT DOCUMENTS

| | | | |
|---|---|---|---|
| 4,678,795 | 7/1987 | Shiokawa et al. | 514/314 |
| 4,742,060 | 5/1988 | Shiokwa et al. | 514/252 |
| 4,774,247 | 9/1988 | Shiokawa et al. | 514/256 |
| 4,812,571 | 3/1989 | Shiokawa et al. | 546/296 |
| 4,831,036 | 5/1989 | Wolf et al. | 514/258 |
| 4,845,106 | 7/1989 | Shiokawa et al. | 514/342 |
| 4,895,850 | 1/1990 | Gesing et al. | 514/258 |
| 4,902,689 | 2/1990 | Gesing et al. | 514/258 |
| 5,001,138 | 3/1991 | Shiokawa et al. | 514/342 |
| 5,204,360 | 4/1993 | Shiokawa et al. | 514/342 |
| 5,298,507 | 3/1994 | Shiokawa et al. | 514/256 |
| 5,428,032 | 6/1995 | Shiokawa et al. | 514/226.8 |
| 5,461,167 | 10/1995 | Shiokawa et al. | 548/202 |
| 5,580,889 | 12/1996 | Shiokawa et al. | 514/343 |
| 5,750,704 | 5/1998 | Shiokawa et al. | 546/275.1 |

FOREIGN PATENT DOCUMENTS

0247477A1 * 12/1987 (EP) .

* cited by examiner

Primary Examiner—Mukund J. Shah
Assistant Examiner—Pavanaram K Sripada
(74) Attorney, Agent, or Firm—Joseph C. Gil

(57) ABSTRACT

The present invention relates to novel tetrahydropyrimidine derivatives of the formula (I)

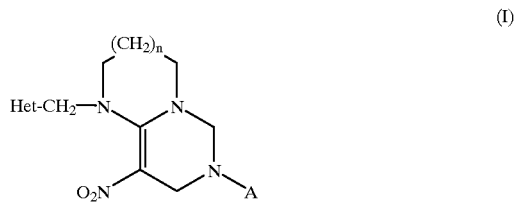

in which
A represents one of the groupings (Ia) —$(CH_2)_m$—$COXR^1$ or (Ib)

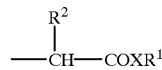

Het represents a five- or six-membered heterocyclic grouping which contains 1, 2, 3 or 4 nitrogen atoms and/or one or two oxygen or sulphur atoms as hetero atom ring members—the number of the ring hetero atoms being 1, 2, 3 or 4—and which is optionally substituted by halogen, cyano, nitro, alkyl, halogenoalkyl, alkenyl, halogenoalkenyl, alkinyl, alkoxy, halogenoalkoxy, alkenyloxy, halogenoalkenyloxy, alkinyloxy, alkylthio, halogenoalkylthio, alkenylthio, halogenoalkenylthio, alkinylthio, alkylsulphinyl, halogenoalkylsulphinyl, alkylsulphonyl, halogenoalkylsulphonyl, amino, alkylamino, dialkylamino, aryl, aryloxy, arylthio, arylamino, aralkyl, formylamino, alkylcarbonylamino, formyl, carbamoyl, alkylcarbonyl and/or alkoxycarbonyl. For other substituents see specification. Process for their preparation and their use as pesticides.

8 Claims, No Drawings

TETRAHYDROPYRIMIDINE DERIVATIVES

This applications is a 371 of PCT/EP97/00775 filed on Feb. 19, 1997.

The present invention relates to novel tetrahydropyrimidine derivatives, processes for their preparation and their use for controlling animal pests.

It is already known that certain bicyclic pyrimidine derivatives, such as, in particular, 6-substituted 6,7-dihydro-8-nitro-(5H)-1-(2-chloropyridin-5-yl-methyl or 2-chloro-1,3-thiazol-5-yl-methyl)-imidazolidino-[2,3-f]-pyrimidines, have insecticidal properties (cf. for example EP-A-0 247 477). However, the activity and the spectrum of action of these compounds is, in particular at low application rates and concentrations, not always entirely satisfactory.

This invention, then, provides novel tetrahydropyrimidine derivatives of the formula (I)

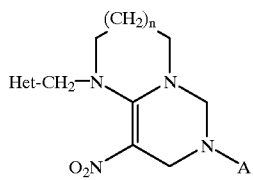
(I)

in which

A represents one of the groupings (Ia) —(CH$_2$)$_m$—COXR$^1$ or

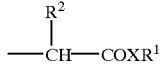
(Ib)

Het represents a five- or six-membered heterocyclic grouping which contains 1, 2, 3 or 4 nitrogen atoms and/or one or two oxygen or sulphur atoms as heteroatom ring members—the number of the ring heteroatoms being 1, 2, 3 or 4—and which is optionally substituted by halogen, cyano, nitro, alkyl, halogenoalkyl, alkenyl, halogenoalkenyl, alkinyl, alkoxy, halogenoalkoxy, alkenyloxy, halogenoalkenyloxy, alkinyloxy, alkylthio, halogenoalkylthio, alkenylthio, halogenoalkenylthio, alkinylthio, alkylsulphinyl, halogenoalkylsulphinyl, alkylsulphonyl, halogenoalkylsulphonyl, amino, alkylamino, dialkylamino, aryl, aryloxy, arylthio, arylamino, aralkyl, formylamino, alkylcarbonylamino, formyl, carbamoyl, alkylcarbonyl and/or alkoxycarbonyl, R$^1$ represents hydrogen, alkyl, halogenoalkyl, alkenyl, halogenoalkenyl, optionally substituted aralkyl or optionally substituted 5- or 6-membered heterocyclylalkyl, R$^2$ represents optionally substituted alkyl or aralkyl, X represents oxygen or the groupings —NH— and —N-alkyl-, m represents integers from 1 to 20 and n represents integers from 0 to 2, but excluding compounds of the formula (I) in which simultaneously A represents the grouping (Ia),
Het represents

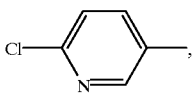

R$^1$ represents hydrogen or ethyl,
X represents oxygen,
m represents 1 or 2 and
n represents 0.

Furthermore, it was found that the tetrahydropyrimidine derivatives of the formula (I) are obtained when a) nitromethylene derivatives of the formula (II)

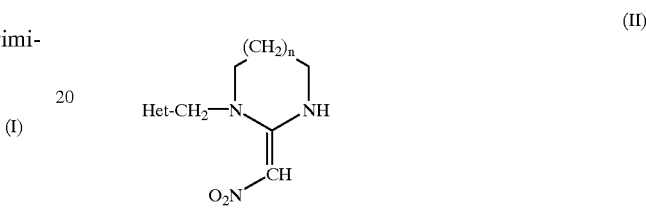
(II)

in which
Het and n are as defined above
are reacted with amines of the formula (IIIa) or (IIIb)

(IIIa)

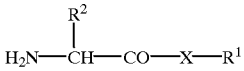
(IIIb)

in which
R$^1$, R$^2$, X and m are as defined above,
optionally in the form of their hydrohalides in the presence of at least twice the molar amount of formaldehyde, if appropriate in the presence of an acid catalyst and if appropriate in the presence of a diluent and if appropriate in the presence of a base;

or b) nitropyrimidine derivatives of the formula (IV)

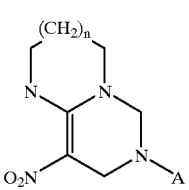
(IV)

in which
A and n are as defined above,
are reacted with compounds of the formula (V)

(V)

in which
Het is as defined above and
L represents an anionic leaving group,
in the presence of a base and, if appropriate, in the presence of a diluent.

Finally, it has been found that the novel tetrahydropyrimidine derivatives of the formula (I) have pronounced biological properties and are especially suitable for controlling animal pests, in particular insects, arachnids and nematodes encountered in agriculture, in forestry, in the protection of stored products and materials, and in the hygiene sector.

Formula (I) provides a general definition of the tetrahydropyrimidine derivatives according to the invention.

Preferred substituents or ranges of the radicals listed in the formulae mentioned hereinabove and hereinbelow will now be illustrated:

Het preferably represents a five- or six-membered grouping from the group consisting of furyl, thienyl, pyrrolyl, pyrazolyl, imidazolyl, 1,2,3- or 1,2,4-triazolyl, oxazolyl, isoxazolyl, 1,2,4- or 1,3,4-oxadiazolyl, thiazolyl, isothiazolyl, 1,2,3-, 1,2,4-, 1,2,5- or 1,3,4-thiadiazolyl, pyridyl, pyridazinyl, pyrimidinyl and pyrazinyl, each of which is optionally mono- or polysubstituted by identical or different substituents from the group consisting of fluorine, chlorine, bromine, iodine, cyano, nitro, $C_1$–$C_4$-alkyl (which is optionally fluorine- and/or chlorine-substituted), $C_2$–$C_4$-alkenyl (which is optionally fluorine- and/or chlorine-substituted), $C_2$–$C_4$-alkinyl, $C_1$–$C_4$-alkoxy (which is optionally fluorine- and/or chlorine-substituted), $C_3$–$C_4$-alkenyloxy (which is optionally fluorine- and/or chlorine-substituted), $C_3$–$C_4$-alkinyloxy, $C_1$–$C_4$-alkylthio (which is optionally fluorine- and/or chlorine-substituted), $C_3$–$C_4$-alkenylthio (which is optionally fluorine- and/or chlorine-substituted), $C_3$–$C_4$-alkinylthio, $C_1$–$C_4$-alkylsulphinyl (which is optionally fluorine- and/or chlorine-substituted), $C_1$–$C_4$-alkylsulphonyl (which is optionally fluorine- and/or chlorine-substituted), amino, $C_1$–$C_4$-alkylamino, di-($C_1$–$C_4$-alkyl)-amino, phenyl, phenoxy, phenylthio, phenylamino, benzyl, formylamino, $C_1$–$C_4$-alkyl, carbonylamino, formyl, carbamoyl, $C_1$–$C_4$-alkyl-carbonyl and/or $C_1$–$C_4$-alkoxy-carbonyl.

$R^1$ preferably represents hydrogen, $C_1$–$C_{12}$-alkyl, $C_1$–$C_6$-halogenoalkyl, $C_2$–$C_6$-alkenyl, or $C_2$–$C_6$-halogenoalkenyl, or phenyl-$C_1$–$C_4$-alkyl optionally substituted by one to five identical or different substituents, suitable phenyl substituents being:

halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, $C_1$–$C_4$-alkoxycarbonyl, amino, $C_1$–$C_4$-alkylamino or di-($C_1$–$C_4$-alkyl)-amino;

or 5- or 6-membered heterocyclyl-$C_1$–$C_4$-alkyl optionally substituted by one to three identical or different substituents, the heterocyclic grouping being from the group consisting of furyl, thienyl, pyrrolyl, pyrazolyl, imidazolyl, 1,2,3- or 1,2,4-triazolyl, oxazolyl, isoxazolyl, 1,2,4- or 1,3,4-oxadiazolyl, thiazolyl, isothiazolyl, 1,2,3-, 1,2,4-, 1,2,5- or 1,3,4-thiadiazolyl, pyridyl, pyridazinyl, pyrimidinyl and pyrazinyl, each of which is optionally mono- to trisubstituted by identical or different substituents from the group consisting of fluorine, chlorine, bromine, iodine, cyano, nitro, $C_1$–$C_4$-alkyl (which is optionally fluorine- and/or chlorine-substituted), $C_2$–$C_4$-alkenyl (which is optionally fluorine- and/or chlorine-substituted), $C_2$–$C_4$-alkinyl, $C_1$–$C_4$-alkoxy (which is optionally fluorine- and/or chlorine-substituted $C_3$–$C_4$-alkenyloxy (which is optionally fluorine- and/or chlorine-substituted), $C_3$–$C_4$-alkinyloxy, $C_1$–$C_4$-alkylthio (which is optionally fluorine- and/or chlorine-substituted), $C_3$–$C_4$-alkenylthio (which is optionally fluorine- and/or chlorine-substituted), $C_3$–$C_4$-alkinylthio, $C_1$–$C_4$-alkylsulphinyl (which is optionally fluorine- and/or chlorine-substituted), $C_1$–$C_4$-alkylsulphonyl (which is optionally fluorine- and/or chlorine-substituted), amino, $C_1$–$C_4$-alkylamino, di-($C_1$–$C_4$-alkyl)-amino, phenyl, phenoxy, phenylthio, phenylamino, benzyl, formylamino, $C_1$–$C_4$-alkyl, carbonylamino, formyl, carbamoyl, $C_1$–$C_4$-alkyl-carbonyl and/or $C_1$–$C_4$-alkoxy-carbonyl.

$R^2$ preferably represents $C_1$–$C_8$-alkyl or optionally substituted benzyl,

X preferably represents oxygen or the groupings —NH— and —N—($C_1$–$C_8$-alkyl)—.

m preferably represents integers from 1 to 12.

n preferably represents the numbers 0 and 1,

There shall be excluded compounds in which simultaneously

A represents the grouping (Ia),

Het represents

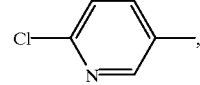

$R^1$ represents hydrogen or ethyl,

X represents oxygen, m represents 1 or 2 and n represents 0.

Het particularly preferably represents a five- or six-membered heterocyclic grouping from the group consisting of pyrazolyl, 1,2,4-triazolyl, oxazolyl, isoxazolyl, thiazolyl, isothiazolyl, 1,2,5-thiadiazolyl, pyridyl, pyrazinyl and pyrimidinyl, each of which is optionally mono- to trisubstituted by identical or different substituents from the group consisting of fluorine, chlorine, bromine, iodine, cyano, nitro, $C_1$–$C_2$-alkyl (which is optionally fluorine- and/or chlorine-substituted), $C_1$–$C_2$-alkoxy (which is optionally fluorine- and/or chlorine-substituted), $C_1$–$C_2$-alkylthio (which is optionally fluorine- and/or chlorine-substituted) and $C_1$–$C_2$-alkylsulphonyl (which is optionally fluorine- and/or chlorine-substituted).

$R^1$ particularly preferably represents hydrogen, $C_1$–$C_8$-alkyl, $C_1$–$C_4$-halogenoalkyl, $C_2$–$C_4$-alkenyl, or $C_2$–$C_4$-halogenoalkenyl, or phenyl-$C_1$–$C_2$-alkyl optionally substituted by one to three identical or different substituents, suitable phenyl substituents being:

fluorine, chlorine, bromine, cyano, nitro, methyl, ethyl, methoxy, methylthio, trifluoromethyl, trifluoromethoxy and trifluoromethylthio;

or 5- or 6-membered heterocyclyl-$C_1$–$C_2$-alkyl optionally substituted by one to three identical or different substituents, the heterocyclic grouping being from the group consisting of pyrazolyl, 1,2,4-triazolyl, oxazolyl, isoxazolyl, thiazolyl, isothiazolyl, 1,2,5-thiadiazolyl, pyridyl, pyrazinyl and pyrimidinyl, each of which is optionally substituted by fluorine, chlorine, bromine, cyano, nitro, $C_1$–$C_2$-alkyl (which is optionally fluorine- and/or chlorine-substituted), $C_1$–$C_2$-alkoxy (which is optionally fluorine- and/or chlorine-substituted), $C_1$–$C_2$-alkylthio (which is optionally fluorine- and/or chlorine-substituted), and $C_1$–$C_2$-alkylsulphonyl (which is optionally fluorine- and/or chlorine-substituted).

$R^2$ particularly preferably represents $C_1$–$C_4$-alkyl or benzyl which is optionally substituted by halogen (chlorine, fluorine, bromine), $C_1$–$C_4$-alkyl, $C_1$–$C_2$-alkoxy, $C_1$–$C_2$-alkylthio, $C_1$–$C_2$-halogenoalkyl, $C_1$–$C_2$-halogenoalkoxy, $C_1$–$C_2$-halogenoalkylthio, nitro, cyano;

X particularly preferably represents oxygen or the groupings —NH—, —N(CH$_3$)— and —N(C$_2$H$_5$)—.
m particularly preferably represents integers from 1 to 10.
n particularly preferably represents the numbers 0 and 1.

There shall be excluded compounds in which simultaneously
A represents the grouping (Ia),
Het represents

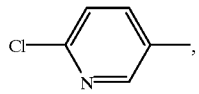

R$^1$ represents hydrogen or ethyl,
X represents oxygen,
m represents 1 or 2 and
n represents 0.
Het very particularly preferably pyridyl and thiazolyl, each of which is optionally substituted by one to two identical or different substituents from the group consisting of fluorine, chlorine and bromine.
R$^1$ very particularly preferably represents hydrogen, C$_1$–C$_8$-alkyl or benzyl which is optionally substituted by one to two identical or different substituents, suitable substituents being:
  fluorine, chlorine, bromine, cyano, nitro, methyl, ethyl, methoxy, methylthio, trifluoromethyl, trifluoromethoxy and trifluoromethylthio;
  or pyridylmethyl and thiazolylmethyl, each of which is optionally substituted by one to two identical or different substituents from the group consisting of fluorine, chlorine or bromine.
R$^2$ very particularly preferably represents C$_1$–C$_4$-alkyl or benzyl;
X very particularly preferably represents oxygen or the —NH— grouping.
m very particularly preferably represents integers from 1 to 8.
n very particularly preferably represents the numbers 0 and 1.

There shall be excluded compounds in which simultaneously
A represents the grouping (Ia),
Het represents

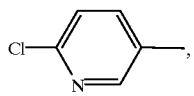

R$^1$ represents hydrogen or ethyl,
X represents oxygen,
m represents 1 or 2 and
n represents 0.

The abovementioned general or preferred definitions of radicals or illustrations apply to the end products and, correspondingly, to the starting materials and intermediates. These radical definitions can be combined with each other as desired, that is to say combinations between the respective preferred ranges are also possible.

Preference according to the invention is given to compounds of the formula (I) which contain a combination of the definitions given above as being preferred (preferable).

Particular preference according to the invention is given to compounds of the formula (I) which contain a combination of the definitions given above as being particularly preferred.

Very particular preference according to the invention is given to compounds of the formula (I) which contain a combination of the definitions given above as being very particularly preferred.

In the radical definitions given hereinabove and hereinbelow, hydrocarbon radicals, such as alkyl or alkenyl, are—also in connection with heteroatoms such as alkoxy or alkylthio—in each case straight-chain or branched as far as this is possible.

Preferred compounds according to the invention are substances of the formulae (Ic) to (If):

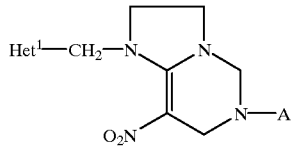

(Ic)

in which
Het$^1$ represents optionally substituted pyridyl and
A is as defined in the definition of the invention.

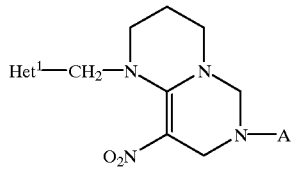

(Id)

in which
Het$^1$ represents optionally substituted pyridyl and
A is as defined in the definition of the invention.

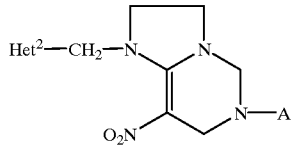

(Ie)

in which
Het$^2$ represents optionally substituted thiazolyl and
A is as defined in the definition of the invention.

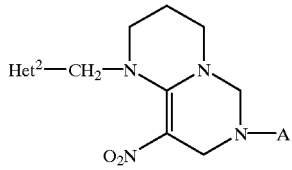

(If)

in which
Het$^2$ represents optionally substituted thiazolyl and
A is as defined in the definition of the invention.

Preferred compounds according to the invention are also substance groups of the formulae (Ia-1), (Ib-1), (Ic-1) and (Id-1):

(Ia-1)

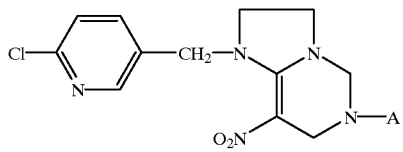

in which
A is generally preferred, particularly preferred and very particularly preferred as defined above.

(Ib-1)

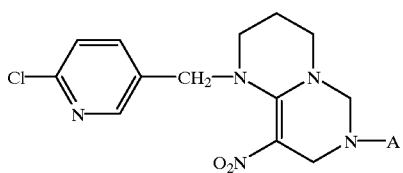

in which
A is generally preferred, particularly preferred and very particularly preferred as defined above.

(Ic-1)

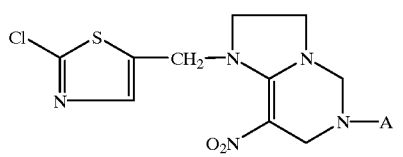

in which
A is generally preferred, particularly preferred and very particularly preferred as defined above.

(Id-1)

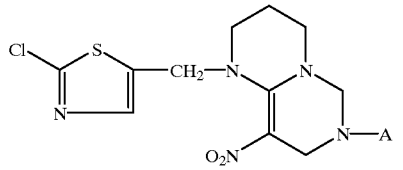

in which
A is generally preferred, particularly preferred and very particularly preferred as defined above.

If, for example, 3-(2-chloropyridin-5-yl-methyl)-2-nitromethylene-imidazolidine, methyl glycinate hydrochloride and 2 mol of formaldehyde are used to carry out the process (a) according to the invention, the course of the reaction may be illustrated by the following scheme:

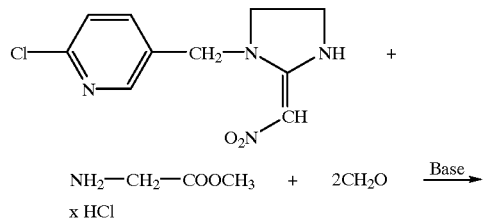

NH$_2$—CH$_2$—COOCH$_3$  +  2CH$_2$O $\xrightarrow{\text{Base}}$
x HCl

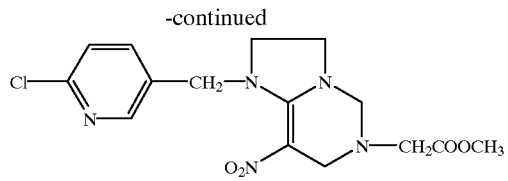

If, for example, 6,7-dihydro-6-methoxycabronylmethyl-8-nitro-(5H)-imidazolidino-[2,3-f]-pyrimidine and 2-chloro-5-chloromethyl-pyridine are used to carry out the process (b) according to the invention, the course of the reaction may be illustrated by the following scheme:

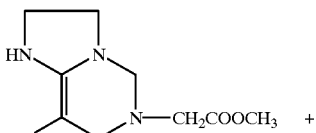

+

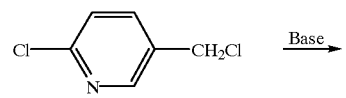

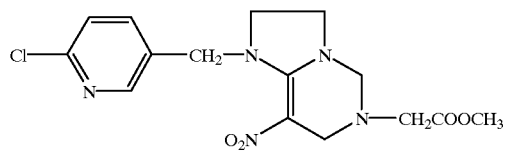

The nitromethylene derivatives of the formula (II) to be used as starting materials in the process (a) according to the invention are known (cf. for example EP-A 0 163 855, EP-A 0 192 060, EP-A 0 247 477, EP-A 0 316 843 and EP-A 0 316 845) and/or may be prepared by known methods (cf. the published European applications mentioned).

If the nitromethylene derivatives are used in the form of their hydrohalides, preference is given to their hydrochlorides.

The amines of the formula (III-a) and (III-b) further to be used as starting materials in the process (a) according to the invention are generally known compounds of organic chemistry and/or can be obtained in a conventional manner.

The nitropyrimidine derivatives of the formula (IV) to be used as starting materials in the process (b) according to the invention have not been disclosed. They can be obtained by reacting nitromethylene derivatives of the formula (IIa) (cf. for example EP-A 0 247 477)

(IIa)

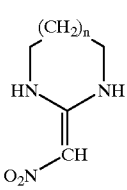

in which
n is as defined above,
with amines of the formula (III-a) and (III-b) using process (a).

The compounds to be additionally used as starting materials in the process (b) according to the invention are defined in a general way by formula (V). L preferably represents chlorine, bromine, iodine, acetoxy, tosyl or mesyl. The compounds of the formula (V) are generally known substances of organic chemistry.

The process (a) according to the invention is preferably carried out using diluents. Suitable diluents are water and organic solvents inert in the reaction. These are preferably aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, alcohols, such as methanol, ethanol, n-propanol and isopropanol. Mixtures of alcohols and water are preferably used.

The process (a) according to the invention is, if appropriate, carried out in the presence of acidic, non-oxidizing catalysts. Hydrohalic acids such as hydrochloric acid and hydrobromic acid, phosphoric acid, and lower carboxylic acids such as acetic acid and propionic acid have proven to be particularly useful.

The reaction temperatures of the process (a) according to the invention may be varied over a relatively wide range. In general, the process is carried out at temperatures between −20° C. and +120° C., preferably at temperatures between 0° C. and +80° C.

The process (a) according to the invention is generally carried out at atmospheric pressure. However, it is also possible to work at elevated or reduced pressure.

When carrying out process (a) according to the invention, 1 to 1.5 mol, preferably 1 to 1.2 mol of amine of the formula (III) and 2 to 4 mol, preferably 2 to 3 mol of formaldehyde are employed per mole of nitromethylene derivative of the formula (II).

The amines of the formula (III) can, if appropriate, be employed as aqueous solutions. If gaseous amines of the formula (III) are used, these compounds can be passed through the mixture of diluent, compound of the formula (II) and formaldehyde. In the process according to the invention, formaldehyde is employed as an aqueous solution. The reactions are generally carried out in a suitable diluent, and the reaction mixture is stirred for several hours at the temperature required in each case. Work-up in the process according to the invention is carried out in each case by customary methods.

The process (b) according to the invention is preferably carried out using diluents. Suitable diluents are virtually all inert organic solvents. These are in particular aliphatic and aromatic, optionally halogenated hydrocarbons, such as, for example, pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone or methyl isobutyl ketone, esters, such as methyl acetate or ethyl acetate, nitriles, such as, for example, acetonitrile or propionitrile, amides, such as, for example, dimethylformamide, dimethylacetamide and N-methylpyrrolidone, and also dimethyl sulphoxide, tetramethylene sulphone or hexamethylphosphoric triamide.

Suitable bases in the processes (a) and (b) according to the invention are all acid binders customarily used for such reactions. Preference is given to alkali metal hydrides and alkaline earth metal hydrides, such as lithium hydride, sodium hydride, potassium hydride or calcium hydride, alkali metal hydroxides or alkaline earth metal hydroxides, such as lithium hydroxide, sodium hydroxide, potassium hydroxide or calcium hydroxide, alkali metal carbonates or hydrogen carbonates or alkaline earth metal carbonates or hydrogen carbonates, such as sodium carbonate or hydrogen carbonate or potassium carbonate or hydrogen carbonate or calcium carbonate, alkali metal acetates, such as sodium acetate or potassium acetate, alkali metal alkoxides, such as sodium tert-butoxide or potassium tert-butoxide, furthermore basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo[4.3.0]-non-5-ene (DBN), 1,8-diazabicyclo-[5.4.0]-undec-7-ene (DBU) or 1,4-diazabicyclo-[2.2.2]-octane (DABCO).

The reaction temperatures in the process (b) according to the invention may be varied over a relatively wide range. Generally, the reaction is carried out at temperatures between 0° C. and 100° C., preferably at temperatures between 10° C. and 80° C.

The process (b) according to the invention is generally carried out at atmospheric pressure. However, it is also possible to work at elevated or reduced pressure.

The starting materials required to carry out process (b) according to the invention are generally employed in roughly equimolar amounts. However, it is also possible to employ one of the two components used in each case in a relatively large excess. The reactions are generally carried out in a suitable diluent in the presence of an acid acceptor, and the reaction mixture is stirred for several hours at the temperature required in each case. Work-up is carried out by customary methods.

The active compounds are suitable for controlling animal pests, in particular insects, arachnids and nematodes, encountered in agriculture, in forestry, in the protection of stored products and of materials, and in the hygiene field, and have good plant tolerance and low toxicity to warm-blooded animals. They may preferably be employed as crop protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci*.

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix*, Pemphigus spp., *Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Spodoptera litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmnannophila pseudospretella, Cacoecia podana, Capua reticulana, Choristoneura furmiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus, Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp.

The phytoparasitic nematodes include, for example, Pratylenchus spp., *Radopholus similis, Ditylenchus dipsaci, Tylenchulus semipenetrans*, Heterodera spp., Globodera spp., Meloidogyne spp., Apelenchoides spp., Longidorus spp., Xiphinema spp., Trichodorus spp.

The compounds of the formula (I) according to the invention in particular have a high insecticidal action.

They can be used particularly successfully for controlling plant-damaging insects, for example against mustard beetle larvae (*Phaedon cochleariae*), caterpillars of the diamond-back moth (*Plutella maculipennis*), the green rice leaf hopper (*Nephotettix cinctriceps*), caterpillars of the owlet moth (*Spodoptera frugiperda*) or green peach aphids (*Myzus persicae*).

The active compounds can be converted to the customary formulations, such as solutions, emulsions, wettable powders, suspensions, powders, dusting agents, pastes, soluble powders, granules, suspension emulsion concentrates, natural and synthetic materials impregnated with active compound and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

Suitable solid carriers are for example ammonium salts and ground natural minerals, such as kaolins, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifying and/or foam-forming agents are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysis products; suitable dispersing agents are: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Examples of particularly advantageous components are the following:

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fihalide, fuberidazole, furalaxyl, firmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclofos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides:

bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:

abamectin, AC 303 630, acephate, acrinathrin, alanycarb, aldicarb, alphamethrin, amitraz, avennectin, AZ 60541, azadirachtin, azinphos A, azinphos M, azocyclotin,

*Bacillus thuringiensis*, bendiocarb, benfuracarb, bensultap, beta-cyfluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, CGA 157419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypernethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimfos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonofos, formothion, fosthiazate, fubfenprox, furathiocarb, HCH, heptenophos, hexaflumuron, hexythiazox, imidacloprid, iprobenfos, isazofos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemeton M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozine, pyrachlofos, pyridaphenthion, pyresmethrin, pyrethrum, pyridaben, pyrimidifen, pyriproxyfen, quinalphos,

RH 5992, salithion, sebufos, silafluofen, sulfotep, sulprofos, tebufenozide, tebufenpyrad, tebupirimifos, teflubenzuron, tefluthrin, temephos, terbam, terbufos, tetrachlorvinphos, thiafenox, thiodicarb, thiofanox, thiometon, thionazin, thuringiensin, tralomethrin, triarathene, triazophos, triazuron, trichlorfon, triflumuron, trimethacarb, vamidothion, XMC, xylylcarb, YI 5301/5302, zetamethrin.

A mixture with other known active ingredients, such as herbicides, or with fertilizers and growth-regulators is also possible.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp. and Solenopotes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp. and Felicola spp.

From the order of the Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopyslla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the sub-class of the Acaria (Acarida) and the orders of the Meta- and Mesostigmata, for example, Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Stemostoma spp. and Varroa spp.

From the order of the Actinedida (Prostigmata) and Acaridida (Astigmata), for example, Acarapis spp., Cheyletiella spp., Omithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

The active compounds of the formula (I) according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, caged birds, aquarium fish, and so-called experimental animals, such as, for example, hamsters, guinea-pigs, rats and mice. By controlling these arthropods, it is intended to reduce deaths and decreased performances (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boluses, the feed-through method, suppositories, by parenteral administration, such as, for example, by means of injections (intramuscular, subcutaneous, intravenous, intraperitoneal and the like), implants, by nasal administration, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10 000, or they may be used in the form of a chemical bath.

Furthermore, it has been found that the compounds of the formula (I) according to the invention have a potent insecticidal action against insects which destroy industrial materials.

The following insects may be mentioned by way of example and as being preferred, but without any limitation:

Beetles, such as

*Hylotrupes bajulus, Chlorophorus pilosis, Anobium punctatum, Xestobium rufovillosum, Ptilinus pecticornis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec., Tryptodendron spec., *Apate monachus, Bostrychus capucins, Heterobostrychus brunneus,* Sinoxylon spec. and *Dinoderus minutus.*

Dermapterans, such as

*Sirex juvencus, Urocerus gigas, Urocerus gigas taignus* and *Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus.*

Bristletails, such as

*Lepisma saccharina.*

Industrial materials are to be understood as meaning, in the present context, non-live materials, such as, preferably, synthetic materials, glues, sizes, paper and board, leather, wood and timber products, and paint.

The materials to be very particularly preferably protected against attack by insects are wood and timber products.

Wood and timber products which can be protected by the composition according to the invention or mixtures comprising such a composition are to be understood as meaning, for example, construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-like solvents having an evaporation number of above 35 and a flashpoint of above 30° C., preferably above 45° C. Substances which are used as such oily and oil-like solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of terpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably a-monochloronaphthalene, are used.

The organic oily or oil-like solvents of low volatility and having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ether, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The artificial resin used as the binder can be employed in the form of an emulsion, dispersion or solution. Up to 10% by weight of bitumen or bituminous substances can also be used as binder. In addition, colorants, pigments, water repellents, odour-masking substances and inhibitors or anti-corrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluene-sulphonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly incorporated into the present application by reference.

Very particularly preferred components which may be admixed are insecticides, such as chlorpyrifos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichiorfluanid, tolylfluanid, 3-iodo-2-propinylbutyl carbamate, N-octyl-isothiazolin-3-one and 4,5-dichloro-N-octylisothiazolin-3-one.

The preparation and the use of the active compounds according to the invention can be seen from the examples which follow.

PREPARATION EXAMPLES

Example 1

(Process a)

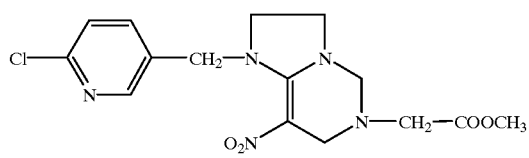

5.0 g (19.6 mmol) of 3-(2-chloropyridin-S-yl-methyl)-2-nitro-methylene-imidazolidine, 3.0 g (23.9 mmol) of methyl glycinate hydrochloride and 3.3 ml of triethylamine together with 3.6 ml of 37% strength formaldehyde solution are dissolved in 30 ml of ethanol and heated under reflux for 5 hours.

The reaction mixture is allowed to cool and concentrated by distilling off the solvent under reduced pressure. The residue is stirred with water, filtered off under suction and dried.

8.9 g of 6,7-dihydro-1-(2-chloropyridin-5-yl-methyl)-6-methoxycarbonyl-methyl-8-nitro-(5H)-imidazolidino-[2,3-f]-pyrimidine of melting point 168° C. are obtained.

Example 2

(Process b)

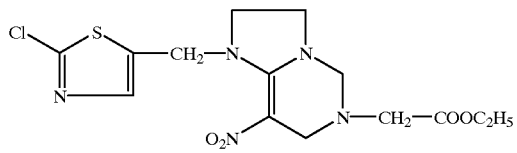

1.5 g (5.86 mmol) of 6,7-dihydro-6-ethoxycarbonyl-methyl-8-(5H)-imidazolidino-[2,3-f]-pyrimidine (Example IV-1) in 20 ml of acetonitrile are treated with 1.6 g of potassium carbonate and 1.0 g (6.0 mmol) of 2-chloro-5-chloromethylthiazole. The reaction mixture is stirred at 40° C. for 6 hours. Insolubles are then filtered off and the solution is evaporated to dryness. The residue is purified by column chromatography.

1.48 g of 6,7-dihydro-1-(2-chlorothiazol-5-yl-methyl)-6-ethoxycarbonyl-methyl-8-nitro-(5H)-imidazolidino-[2,3-f]-pyrimidine of melting point 151° C. are obtained.

Preparation of the starting material (IV-1)

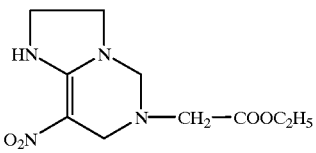

2.0 g (20.2 mmol) of 2-nitromethylene-imidazolidine in 30 ml of ethanol are admixed with 2.8 g (20.1 mmol) of ethyl glycinate hydrochloride, 2.7 ml of triethylamine and 4 ml of 37% strength aqueous formaldehyde solution and heated under reflux for 10 hours. The reaction mixture is allowed to cool and concentrated by distilling off the solvent. The residue is partitioned between water and diethyl ether, the organic phase is separated off, dried over sodium sulphate and concentrated.

2.0 g of 6,7-dihydro-6-ethoxycarbonylmethyl-8-nitro-(5H)-imidazolidino-[2,3-f]-pyrimidine of melting point 155–158° C. are obtained.

By the methods of Examples 1 and 2 and according to the general preparation instructions, the compounds of the formula (I) listed in the Table 1 below are obtained:

TABLE 1

Het—CH$_2$—N structure with (CH$_2$)$_n$, O$_2$N, and A substituents

A represents (CH$_2$)$_m$-COXR$^1$

| Ex. No. | Het | n | m | X | R$^1$ | mp (° C.) or Lg. P*) |
|---|---|---|---|---|---|---|
| 3 | 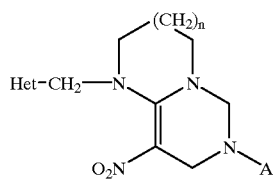 | 0 | 1 | NH | phenyl | 235 |

TABLE 1-continued

Het—CH$_2$—N ring system with (CH$_2)_n$, O$_2$N, and N—A substituents

A represents (CH$_2)_m$-COXR$^1$

| Ex. No. | Het | n | m | X | R$^1$ | mp (° C.) or Lg. P*) |
|---|---|---|---|---|---|---|
| 4 | 6-chloropyridin-3-yl | 0 | 5 | O | H | 1.07 |
| 5 | 6-chloropyridin-3-yl | 0 | 3 | O | C$_2$H$_5$ | 0.94 |
| 6 | 2-chloro-5-methylthiazol-... | 0 | 1 | O | CH$_3$ | 195 |
| 7 | 6-chloropyridin-3-yl | 0 | 1 | O | (6-chloropyridin-3-yl)CH$_2$— | 132 |
| 8 | 6-chloropyridin-3-yl | 0 | 1 | O | sec-butyl (CH$_3$CH$_2$CH(CH$_3$)—) | 145 |
| 9 | 6-chloropyridin-3-yl | 0 | 1 | O | isopropyl ((CH$_3$)$_2$CH—) | 146 |
| 10 | 6-chloropyridin-3-yl | 0 | 1 | O | 4-methylbenzyl | 137 |
| 11 | 6-chloropyridin-3-yl | 0 | 1 | O | C$_8$H$_{17}$-n | 128 |
| 12 | 6-chloropyridin-3-yl | 0 | 1 | O | 3,4-dichlorobenzyl | 150 |
| 13 | 6-chloropyridin-3-yl | 0 | 1 | O | 2,6-dichlorobenzyl | 176 |

TABLE 1-continued

[Structure: Het-CH₂-N bonded in a bicyclic ring system with (CH₂)ₙ bridge, O₂N substituent, and N-A group]

A represents $(CH_2)_m\text{-}COXR^1$

| Ex. No. | Het | n | m | X | R¹ | mp (° C.) or Lg. P*) |
|---|---|---|---|---|---|---|
| 14 | 2-Cl-pyridin-5-yl | 0 | 1 | O | 2,4-dichlorobenzyl | 130 |
| 15 | 2-Cl-pyridin-5-yl | 0 | 3 | O | CH₃ | 1.12 |
| 16 | 2-Cl-5-methylthiazol-yl | 0 | 3 | O | CH₃ | 1.13 |
| 17 | 2-Cl-5-methylthiazol-yl | 0 | 3 | O | C₂H₅ | 1.35 |
| 18 | 2-Cl-pyridin-5-yl | 0 | 1 | NH | 4-(C₂H₅OOC)-phenyl | 165 |
| 19 | 2-Cl-pyridin-5-yl | 0 | 4 | O | CH₃ | 130 |
| 20 | 2-Cl-5-methylthiazol-yl | 0 | 7 | O | CH₃ | 112 |
| 21 | 2-Cl-pyridin-5-yl | 0 | 7 | O | CH₃ | 1.73 |
| 22 | 2-Cl-pyridin-5-yl | 0 | 1 | NH | 4-(C₂H₅OOC)-phenyl | 150 |
| 23 | 2-Cl-pyridin-5-yl | 0 | 2 | O | isopropyl | 1.51 |
| 24 | 2-Cl-pyridin-5-yl | 0 | 4 | O | sec-butyl | 1.47 |

TABLE 1-continued $$\text{Het—CH}_2\text{—N} \begin{array}{c} (CH_2)_n \\ \diagup \\ N \\ \diagdown \\ \end{array} \text{N—A}$$

with $O_2N$ substituent

A represents $(CH_2)_m$-COXR$^1$

| Ex. No. | Het | n | m | X | R$^1$ | mp (° C.) or Lg. P*⁾ |
|---|---|---|---|---|---|---|
| 25 | 2-Cl-pyridin-5-yl | 0 | 1 | NH | H | 195 |
| 26 | 2-Cl-pyridin-5-yl | 0 | 2 | O | CH$_3$ | 108 |

*⁾Lg. P = Logarithm of the partition coefficient P of the substance between the solvents octanol and water, determined experimentally by reversed phase HPLC.

Compounds of the formula I

A represents $-\underset{\underset{\text{CH}}{|}}{\overset{R^2}{|}}-\text{COXR}^1$    30

| Ex. No. | Het | R$^2$ | —COXR$^1$ | mp (° C.) or Lg. P*⁾ |
|---|---|---|---|---|
| 27 | 2-Cl-pyridin-5-yl | —CH$_2$—C$_6$H$_5$ | COOC$_2$H$_5$ | 1.99 |
| 28 | 2-Cl-pyridin-5-yl | —C$_3$H$_7$-i | COOCH$_3$ | 1.55 |
| 29 | 2-Cl-pyridin-5-yl | CH$_3$ | COOCH$_3$ | |
| 30 | 2-Cl-pyridin-5-yl | CH$_2$C$_3$H$_7$-i | COOC$_2$H$_5$ | |
| 31 | 2-Cl-pyridin-5-yl | CH(CH$_3$)C$_2$H$_5$ | COOCH$_3$ | |

By the method of Example 2 and according to the general preparation instructions, the starting materials of the formula (IV) listed in Table 2 below are obtained:

TABLE 2

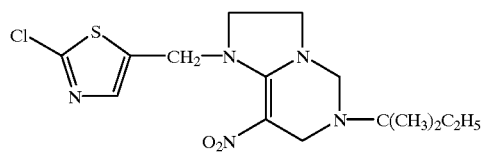

(IV)

| Ex. No. | n | m | X | R$^1$ | Physical constants |
|---|---|---|---|---|---|
| IV-2 | 0 | 1 | O | CH$_3$ | mp. 183–85° C. |

USE EXAMPLES

In the following use examples, the compounds listed below are employed as reference compounds:

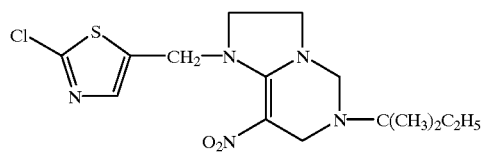
(A)

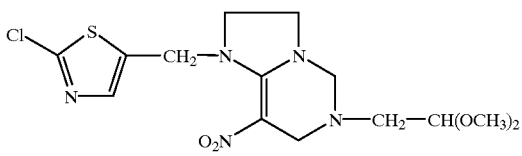
(B)

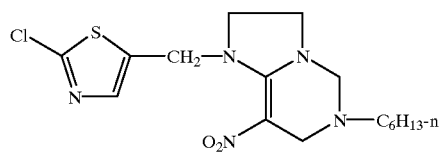
(C)

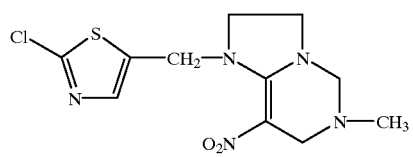
(D)

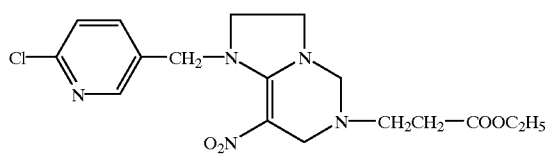
(E)

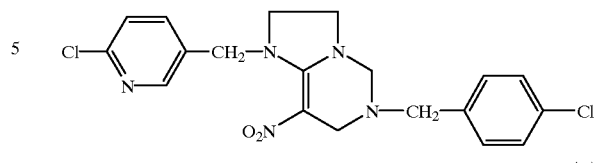
(F)

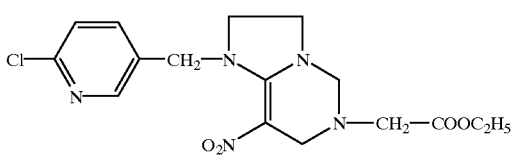
(G)

(all compounds are disclosed in EP-A 0 247 477)

Example A

Phaedon larvae test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*) while the leaves are still moist.

After the specified period of time, the destruction in % is determined. 100% means that all the beetle larvae have been killed; 0% means that none of the beetle larvae have been killed.

In this test, a destruction of 100% was brought about, in each case after 3 days, for example by the compounds of Preparation Examples 1, 3, 4, 7, 9, 10, 11, 12, 14, 19, 20, 22 and 23 at an exemplary active compound concentration of 0.001%, while the known compounds (A), (B), (C) and (E) exhibited no action, a destruction of only 30%, a destruction of only 40% and a destruction of only 20%, respectively.

Example B

Plutella test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with caterpillars of the diamondback moth (*Plutella maculipennis*) while the leaves are still moist.

After the specified period of time, the destruction in % is determined. 100% means that all the caterpillars have been killed; 0% means that none of the caterpillars have been killed.

In this test, a destruction of 100% was brought about, in each case after 3 days, for example by the compounds of Preparation Examples 1, 6, 8, 9, 10, 11, 12, 13, 14, 15, 17, 19, 21 and 22 at an exemplary active compound concentration of 0.01%, while the known compound (E) exhibited no action.

Example C

*Spodoptera frugiperda* test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with caterpillars of the owlet moth (*Spodoptera frugiperda*) while the leaves are still moist.

After the specified period of time, the action in % is determined. 100% means that all the caterpillars have been killed; 0% means that none of the caterpillars have been killed.

In this test, a destruction of 100% was brought about, in each case after 3 days, for example by the compounds of Preparation Examples 8, 9, 10, 11, 12, 14, 15, 19 and 20 at an exemplary active compound concentration of 0.001%, while the known compounds (A), (D) and (F) exhibited no action and (B), (C) and (G) brought about a destruction of only 30%.

Example D

Nephotettix test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of the active compound of the desired concentration and are infested with larvae of the green rice leaf hopper (*Nephotettix cincticeps*) while the seedlings are still moist.

After the desired period of time, the destruction in % is determined. 100% means that all the leaf hoppers have been killed; 0% means that none of the leaf hoppers have been killed.

In this test, a destruction of 100% was brought about, in each case after 6 days, for example by the compounds of Preparation Examples 6, 7, 8, 9, 10, 14, 15, 16, 17 and 18 at an exemplary active compound concentration of 0.0001%, while the known compound (E) brought about a destruction of only 20%.

Example E

Myzus test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Broad bean seedlings (*Vicia faba*) infested with green peach aphids (*Myzus persicae*) are dipped into the preparation of the active compound of the desired concentration and placed into a plastic dish.

After the specified period of time, the destruction in % is deter-mined. 100% means that all the aphids have been killed; 0% means that none of the aphids have been killed.

In this test, the following destructions were brought about by the compounds of the following preparation examples: 1=99%, 4=80%, 6 and 16=90%, 15=98%, 19=95% and 20=100%, in each case after 1 day, at an exemplary active compound concentration of 0.001%, while the known compounds (E) and (F) exhibited a destruction of only 10% and no action, respectively.

What is claimed is:

1. A tetrahydropyrimidine derivative of the formula (I)

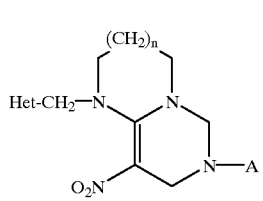

(I)

in which

A represents one of the groupings (Ia) —$(CH_2)_m$—$COXR^1$ or (Ib)

Het represents a five- or six-membered grouping selected from the group consisting of furyl, thienyl, pyrrolyl, pyrazolyl, imidazolyl, 1,2,3- or 1,2,4-triazolyl, oxazolyl, isoxazolyl, 1,2,4- or 1,3,4-oxadiazolyl, thiazolyl, isothiazolyl, 1,2,3-, 1,2,4-, 1,2,5- or 1,3,4-thiadiazolyl, pyridyl, pyridazinyl, pyrimidinyl and pyrazinyl, each of which is unsubstituted or mono- or polysubstituted by identical or different substituents selected from the group consisting of fluorine, chlorine, bromine, iodine, cyano, nitro, unsubstituted or fluorine- and/or chlorine-substituted $C_1$–$C_4$-alkyl, unsubstituted or fluorine- and/or chlorine-substituted $C_2$–$C_4$-alkenyl, unsubstituted or fluorine- and/or chlorine-substituted $C_2$–$C_4$-alkinyl, unsubstituted or fluorine- and/or chlorine-substituted $C_1$–$C_4$-alkoxy, unsubstituted or fluorine- and/or chlorine-substituted $C_3$–$C_4$-alkenyloxy, $C_3$–$C_4$-alkinyloxy, unsubstituted or fluorine- and/or chlorine-substituted $C_1$–$C_4$-alkylthio, unsubstituted or fluorine- and/or chlorine-substituted $C_3$–$C_4$-alkenylthio, unsubstituted or fluorine- and/or chlorine-substituted $C_3$–$C_4$-alkinylthio, unsubstituted or fluorine- and/or chlorine-substituted $C_1$–$C_4$-alkylsulphinyl, unsubstituted or fluorine- and/or chlorine-substituted $C_1$–$C_4$-alkylsulphonyl, amino, $C_1$–$C_4$-alkylamino, di-($C_1$–$C_4$-alkyl)-amino, phenyl, phenoxy, phenylthio, phenylamino, benzyl, formylamino, $C_1$–$C_4$-alkyl, carbonylamino, formyl, carbamoyl, $C_1$–$C_4$-alkyl-carbonyl and/or $C_1$–$C_4$-alkoxy-carbonyl, $R^1$ represents $C_1$–$C_6$-halogenoalkyl, $C_2$–$C_6$-alkenyl, or $C_2$–$C_8$-halogenoalkenyl, or phenyl-$C_1$–$C_4$-alkyl unsubstituted or substituted by one to five identical or different substituents selected from halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, $C_1$–$C_4$-alkoxycarbonyl, amino, $C_1$–$C_4$-alkylamino or di-($C_1$–$C_4$-alkyl)-amino; or 5- or 6-membered heterocyclyl-$C_1$–$C_4$-alkyl unsubstituted or substituted by one to three identical or different substituents, the heterocyclic grouping being selected from the group consisting of furyl, thienyl, pyrrolyl, pyrazolyl, imidazolyl, 1,2,3- or 1,2,4-triazolyl, oxazolyl, isoxazolyl, 1,2,4- or 1,3,4-oxadiazolyl, thiazolyl, isothiazolyl, 1,2,3-, 1,2,4-, 1,2,5- or 1,3,4-thiadiazolyl, pyridyl, pyridazinyl, pyrimidinyl and pyrazinyl, each of which is unsubstituted or mono- to trisubstituted by identical or different substituents from the group consisting of fluorine, chlorine, bromine, iodine, cyano, nitro, unsubstituted or fluorine- and/or chlorine-substituted $C_1$–$C_4$-alkyl, unsubstituted or fluorine- and/or chlorine-substituted $C_2$–$C_4$-alkenyl, $C_2$–$C_4$-alkinyl, unsubstituted or fluorine- and/or chlorine-substituted $C_1$–$C_4$-alkoxy, unsubstituted or fluorine- and/or chlorine-substituted $C_3$–$C_4$-alkenyloxy, $C_3$–$C_4$-alkinyloxy, unsubstituted or fluorine- and/or chlorine-substituted $C_1$–$C_4$-alkylthio, unsubstituted or fluorine- and/or chlorine-substituted $C_3$–$C_4$-alkenylthio, $C_3$–$C_4$-alkinylthio, unsubstituted or fluorine- and/or chlorine-substituted $C_1$–$C_4$-alkylsulphinyl, unsubstituted or fluorine- and/or chlorine-substituted $C_1$–$C_4$-alkylsulphonyl, amino, $C_1$–$C_4$-alkylamino, di-($C_1$–$C_4$-alkyl)-amino, phenyl, phenoxy, phenylthio, phenylamino, benzyl, formylamino, $C_1$–$C_4$-alkyl, carbonylamino, formyl, carbamoyl, $C_1$–$C_4$-alkyl-carbonyl and/or $C_1$–$C_4$-alkoxy-carbonyl, $R^2$ represents $C_1$–$C$,-alkyl or benzyl or substituted benzyl, X represents oxygen or the groupings —NH— and —N—($C_1$–$C_8$-alkyl)—, m represents integers from 1 to 12, and n represents the numbers 0 and 1.

2. A process for preparing the tetrahydropyrimidine derivative of the formula (I) according to claim 1

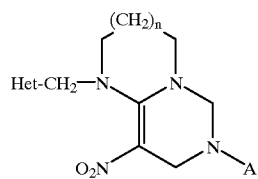

(I)

wherein

A represents one of the groupings (Ia) —$(CH_2)_m$—$COXR^1$ or (Ib)

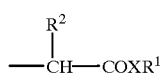

Het represents a five- or six-membered heterocyclic grouping which contains 1, 2, 3 or 4 nitrogen atoms and/or one or two oxygen or sulphur atoms as hetero atom ring members—the number of the ring hetero atoms being 1, 2, 3 or 4—and which is optionally substituted by halogen, cyano, nitro, alkyl, halogenoalkyl, alkenyl, halogenoalkenyl, alkinyl, alkoxy, halogenoalkoxy, alkenyloxy, halogenoalkenyloxy, alkinyloxy, alkylthio, halogenoalkylthio, alkenylthio, halogenoalkenylthio, alkinylthio, alkylsulphinyl, halogenoalkylsulphinyl, alkylsulphonyl, halogenoalkylsulphonyl, amino, alkylamino, dialkylamino, aryl, aryloxy, arylthio, arylamino, aralkyl, formylamino, alkylcarbonylamino, formyl, carbamoyl, alkylcarbonyl and/or alkoxycarbonyl, $R^1$ represents hydrogen, alkyl, halogenoalkyl, alkenyl, halogenoalkenyl, optionally substituted aralkyl or optionally substituted 5- or 6-membered heterocyclylalkyl, $R^2$ represents optionally substituted alkyl or aralkyl, X represents oxygen or the groupings —NH— and —N-alkyl-, m represents integers from 1 to 20 and n represents the integer 0, but excluding compounds in which simultaneously A represents the grouping (Ia), Het represents

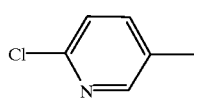

$R^1$ represents hydrogen or ethyl,

X represents oxygen, m represents 1 or 2 and n represents 0, comprising reacting a) a nitromethylene derivative of the formula (II)

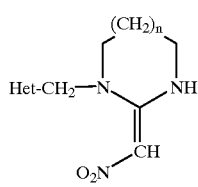

(II)

in which

Het and n are as defined above are reacted with amines of the formula (IIIa) or (IIIb)

$H_2N$—$(CH_2)_m$—$CO$—$X$—$R^1$ (IIIa)

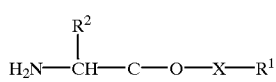 (IIIb)

wherein $R^1$, $R^2$, X and m are as defined above, optionally in the form of their hydrohalides in the presence of at least twice the molar amount of formaldehyde, optionally in the presence of an acid catalyst and optionally in the presence of a diluent and if appropriate in the presence of a base.

3. A method for controlling pests comprising applying tetrahydropyrimidines of the formula (I) according to claim 1 on the pests and/or their habitat.

4. A process for preparing pesticides comprising mixing tetrahydropyrimidines of the formula (I) according to claim 1 with extenders and/or surface-active agents.

5. A pesticide formulation comprising at least one tetrahydropyrimidine of the formula (I) according to claim 1 and extenders and/or surface-active agents.

6. The compound of formula (I) according to claim 1

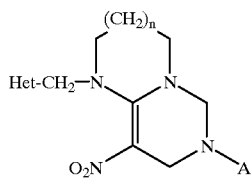

(I)

in which

A represents one of the groupings (Ia) —$(CH_2)_m$—$COXR^1$ or (Ib)

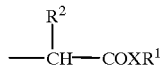

Het represents a five- or six-membered heterocyclic grouping from the group consisting of pyrazolyl, 1,2,4-triazolyl, oxazolyl, isoxazolyl, thiazolyl, isothiazolyl, 1,2,5-thiadiazolyl, pyridyl, pyrazinyl and pyrimidinyl, each of which is unsubstituted or mono- to trisubstituted by identical or different substituents from the group consisting of fluorine, chlorine, bromine, iodine, cyano, nitro, unsubstituted or fluorine- and/or chlorine-substituted $C_1$–$C_2$-alkyl, unsubstituted or fluorine- and/or chlorine-substituted $C_1$–$C_2$-alkoxy, unsubstituted or fluorine- and/or chlorine-substituted $C_1$–$C_2$-alkylthio, and unsubstituted or fluorine- and/or chlorine-substituted $C_1$–$C_2$-, $R^1$ represents $C_1$–$C_4$-halogenoalkyl, $C_2$–$C_4$-alkenyl, or $C_2$–$C_4$-halogenoalkenyl, or phenyl-$C_1$–$C_2$-alkyl unsubstituted or substituted by one to three identical or different substituents selected from: fluorine, chlorine, bromine, cyano, nitro, methyl, ethyl, methoxy, methylthio, trifluoromethyl, trifluoromethoxy and trifluoromethylthio; or 5- or 6-membered heterocyclyl-$C_1$–$C_2$-alkyl unsubstituted or substituted by one to three identical or different substituents, the heterocyclic grouping being from the group consisting of pyrazolyl, 1,2,4-triazolyl, oxazolyl, isoxazolyl, thiazolyl, isothiazolyl, 1,2,5-thiadiazolyl, pyridyl, pyrazinyl and pyrimidinyl, each of which is unsubstituted or substituted by fluorine, chlorine, bromine, cyano, nitro, unsubstituted or fluorine- and/or chlorine-substituted $C_1$–$C_2$-alky, unsubstituted or fluorine- and/or chlorine-substituted $C_1$–$C_2$-alkoxy, unsubstituted or fluorine- and/or chlorine-substituted $C_1$–$C_2$-alkylthio, and unsubstituted or fluorine- and/or chlorine-substituted $C_1$–$C_2$-alkylsulphonyl, $R^2$ represents $C_1$–$C_4$-alkyl, or benzyl which is unsubstituted or substituted by halogen selected from chlorine, fluorine, and bromine; $C_1$–$C_4$-alkyl, $C_1$–$C_2$-alkoxy, $C_1$–$C_2$-alkylthio, $C_1$–$C_2$-halogenoalkyl, $C_1$–$C_2$-halogenoalkoxy, $C_1$–$C_2$-halogenoalkylthio, nitro, cyano, X represents oxygen or the groupings —NH—, —N($CH_3$)— and —N($C_2H_5$)—, m represents integers from 1 to 10 and n represents the numbers 0 and 1.

7. The compound of claim 1 wherein

Het represents pyridyl and thiazolyl, each of which is unsubstituted or substituted by one to two identical or different substituents from the group consisting of fluorine, chlorine and bromine, $R^1$ represents benzyl which is unsubstituted or substituted by one to two identical or different substituents selected from: fluorine, chlorine, bromine, cyano, nitro, methyl, ethyl, methoxy, methylthio, trifluoromethyl, trifluoromethoxy and trifluoromethylthio; or pyridylmethyl and thiazolylmethyl, each of which is unsubstituted or substituted by one to two identical or different substituents from the group consisting of fluorine, chlorine, or bromine, $R^2$ represents $C_1$–$C_4$-alkyl or benzyl, X represents oxygen or the —NH— grouping, m represents integers from 1 to 8, and n represents the numbers 0 and 1.

8. The compound of claim 1 wherein Het is thiozolyl or pyridyl.

* * * * *